United States Patent [19]

Oppenlander et al.

[11] Patent Number: 5,737,445
[45] Date of Patent: Apr. 7, 1998

[54] AUTOMATED FEATURE DETECTION AND IDENTIFICATION IN DIGITAL POINT-ORDERED SIGNALS

[75] Inventors: Jane E. Oppenlander, Burnt Hills; Kent C. Loomis, Clifton Park; David M. Brudnoy, Albany; Arthur J. Levy, Schenectady, all of N.Y.

[73] Assignee: The United States of America as represented by the United States Department of Energy, Washington, D.C.

[21] Appl. No.: 425,758

[22] Filed: Apr. 20, 1995

[51] Int. Cl.⁶ .............................. G06K 9/46; G06F 15/46
[52] U.S. Cl. .................... 382/207; 324/236; 364/550; 364/506; 364/571.01
[58] Field of Search .......................... 364/506, 550, 364/571.01, 481; 324/238, 236, 233; 382/149, 207, 141; 250/461.1; 395/916, 908

[56] References Cited

U.S. PATENT DOCUMENTS

| | | | |
|---|---|---|---|
| 4,207,520 | 6/1980 | Flora et al. | 324/238 |
| 4,763,274 | 8/1988 | Junker et al. | 364/481 |
| 5,121,443 | 6/1992 | Tomlinson | 382/207 |
| 5,339,256 | 8/1994 | Levy et al. | 364/506 |
| 5,345,514 | 9/1994 | Mahdavieh et al. | 382/207 |
| 5,420,787 | 5/1995 | Gawne et al. | 382/207 |
| 5,432,862 | 7/1995 | Hirsch | 382/207 |
| 5,570,431 | 10/1996 | Gillard et al. | 382/149 |
| 5,627,910 | 5/1997 | Gachet et al. | 382/141 |

*Primary Examiner*—Leo Boudreau
*Assistant Examiner*—Bhavesh Mehta
*Attorney, Agent, or Firm*—Virginia B. Caress; William R. Moser; Paul A. Gottlieb

[57] ABSTRACT

A computer-based automated method to detect and identify features in digital point-ordered signals. The method is used for processing of non-destructive test signals, such as eddy current signals obtained from calibration standards. The signals are first automatically processed to remove noise and to determine a baseline. Next, features are detected in the signals using mathematical morphology filters. Finally, verification of the features is made using an expert system of pattern recognition methods and geometric criteria. The method has the advantage that standard features can be, located without prior knowledge of the number or sequence of the features. Further advantages are that standard features can be differentiated from irrelevant signal features such as noise, and detected features are automatically verified by parameters extracted from the signals. The method proceeds fully automatically without initial operator set-up and without subjective operator feature judgement.

23 Claims, 13 Drawing Sheets

AUTOMATED FEATURE DETECTION AND IDENTIFICATION IN DIGITAL POINT-ORDERED SIGNALS

FIELD OF THE INVENTION

The present invention relates to computer-based automated processing of digital point-ordered signals. Further it relates to computer-based automated processing of non-destructive test signals, used in testing of material parts. More particularly it relates to processing of signals where features present in the signals are known in advance, as occurs for calibration signals. It is particularly useful for processing eddy current (ET) calibration signals.

BACKGROUND AND SUMMARY OF THE INVENTION

Non-destructive methods, used to inspect materials for flaws or for other material discontinuities in a test piece, typically involve radiative transmission over areas suspected of containing flaws and reception of a signal in response to this transmission. If patterns in the received signal due to flaws are sufficiently distinct from other signal features, then material flaws can be revealed. The processing of signals is often performed by human analysts, who visually inspect signals in search of those patterns caused by flaws.

Eddy current testing (ET), used to inspect metallic parts, is one example of a non-destructive inspection method. It involves the use of an electromagnetic probe with a coil, or coils, that moves across the surface of a test piece, inducing electrical currents (eddy currents) in the test piece near the probe. Since discontinuities in a metal (such as a flaw) can alter the flow of eddy currents, thereby changing the electromagnetic impedance of the coil, measurement of probe impedance can provide the information needed to locate and identify discontinuities in the material.

In order to accurately locate and quantify the nature of flaws, a test system usually must be calibrated. For ET testing, calibration is performed by passing a probe over the surface of a calibration standard that contains known material features. For example, it may include drilled holes of different depths, as well as bends, dents, bulges, or externally placed structural members.

During an actual inspection many calibration measurements may be necessary as a check on system stability. Even though each calibration measurement is performed on a standard calibration piece, variations can occur from one run to the next. Sometimes one calibration run will be performed with the probe moving in one direction along the calibration piece, and at other times the probe will move in another direction. Sometimes a calibration piece may consist of different pieces connected together, with different sequences of connected pieces occurring from one run to the next. In both these cases, signal pattern sequencing may change from run to run. Also sometimes a calibration run will not include all possible features, and this information may not be known to an analyst before processing takes place. The human visual system is sufficiently sophisticated, however, so that a trained analyst can usually detect sequence change, or pattern absence, in a signal produced by a standard calibration piece.

The present invention is a computer-based method that automates the processing of the above-described signals by emulating the capabilities of a human analyst. Specifically, the computer-based automated system of this invention provides:

automatic identification of regions of the signal that contain patterns of interest;

automatic identification of signal background levels in regions of interest;

automatic identification of patterns of interest regardless of sequence in a digital, point-ordered signal;

automatic identification of patterns of interest without a priori knowledge of the number of patterns present in a signal.

The methods put forward in this invention will be exemplified by a preferred embodiment, processing of eddy current (ET) calibration signals taken from inspection of heat exchanger tubing. However, the methods claimed here can be applied generally to the automatic processing of any digital point-ordered signal, or set of signals, containing known, mutually distinguishable signal patterns. Many non-destructive techniques produce signals of this type; examples are found in acoustic emission, noise monitoring, and ultrasonics.

It is an object of this invention to provide a process which automatically identifies signal features in digital, point-ordered signals, in which all possible features are known in advance, e.g. in calibration.

It is also an object of the invention to automatically detect and locate standard features without knowing a priori the number of features present or the sequence in which they occur.

It is a further object of this invention to provide a process which automatically identifies signal features in eddy current testing calibration data, without operator intervention.

It is another object of the invention to provide an automated process for eddy current calibration that identifies featureless regions of the test piece.

It is a further object of the invention to provide an automated process for eddy current calibration that differentiates standard calibration features from irrelevant signal features, such as that produced by noise.

It is a further object of the invention to provide an automated process for eddy current calibration that verifies detected features based on examination of parameters extracted from the signal.

BRIEF DESCRIPTION OF THE DRAWINGS

FIG. 5(a) is a plot of an eddy current signal of the lowest frequency impedance amplitude;

FIG. 5(b) is an enlargement of the boxed area in FIG. 5(a), which is the ring/5-hole section;

FIG. 5(c) shows the signal of 5(b) after filtering (original signal [dashed] and filtered signal [solid]);

FIG. 5(d) shows replacement of the ring peak with a quadratic "cap";

FIG. 5(e) shows the signal of FIG. 5(b) at higher frequency with the ring peak removed (original signals [dashed] and filtered signals [solid]);

FIG. 5(f) shows the processed signal of FIG. 5(e) with 5 quadratic peaks;

DETAILED DESCRIPTION OF THE INVENTION

Figure 1A:
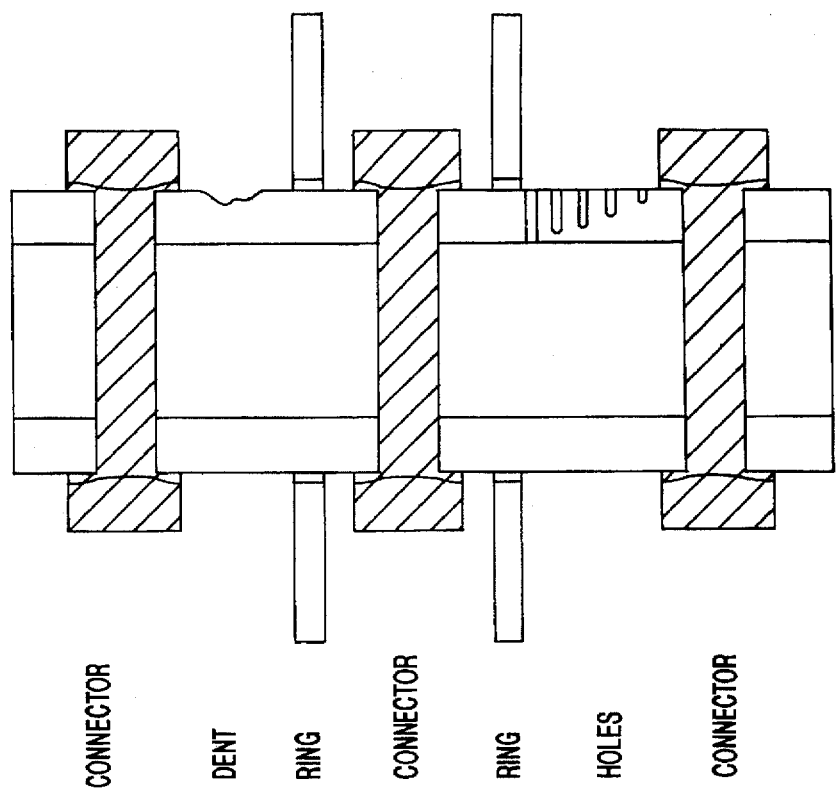
FIG. 1(a) is a schematic representation of an axial-cross-sectional cut of a tube calibration piece and the corresponding horizontal and vertical components of the eddy current signals for those features shown.

It is an advantage Of this invention that it proceeds fully automatically without initial operator set-up and without subjective operator feature judgement.

It is an advantage of this invention that it locates features independent of the physical layout of the calibration standard, using methods that emulate the visual approach of a human analyst.

It is also an advantage that the invention contains a method for feature detection and discrimination that adapts to local levels of noise in the signal.

Other features and advantages of the present invention are stated in or are apparent from a detailed description of presently preferred embodiments of the invention found herein below.

A. Introduction

This invention is a novel process that makes use of certain distinguishing features of digital point-ordered signals by applying combinations of analytic tools from a variety of technologies including mathematical morphology and pattern recognition. The process is composed of three major components—signal pre-processing, feature detection; and feature verification. Each of these three components is described in detail below. It should be made clear that feature detection and verification, as used herein, refers to features in the signal being processed, wherein these signal features represent the response of measurement instruments to physical features in the test material.

B. Signal Pre-processing

The method of the invention is best described using a preferred embodiment of eddy current calibration signals from a heat exchanger calibration tube. The signals obtained can be input directly to a digital computer, or stored on a storage device, such as magnetic tape or optical disk, and input to a computer at a later time. In the preferred embodiment described herein, the calibration signals were input from a storage device to a digital computer. This method has been implemented on four different types of computers—Digital Equipment Corporation VAX station workstation, Digital Equipment Corporation VAX minicomputer, Hewlett Packard 9000/400 workstation, and Hewlett Packard 9000/700 workstation. However, implementation of this method is not limited to these computer platforms.

Signal pre-processing is performed for two reasons. First, unwanted noise is removed, whose presence might otherwise confound the detection processes. Second, an accurate baseline is determined, corresponding to the null value of the probe; significant deviations of the signal from the baseline position are indications of features of interest. By null value is meant the value of the signal recorded by the measuring instrument in regions where no features of interest are present.

An eddy current dual bobbin probe measures electromagnetic impedance, $Z_k(f)=(R_k(f),Y_k(f))$, at N points $(k=1,2,\ldots,N)$ along the test piece; $R_k(f)$ is called the resistive component and $Y_k(f)$ the reactive component of impedance $Z_k(f)$ at point k. The dependence of $Z_k(f)$, on eddy current generation frequency, f, is related to spatial range. As f decreases, the spatial penetration most sensitive to measurement increases, and vice-versa. Common practice is to measure the impedance signal, $Z_k(f)$ at several frequencies in order to best investigate the entire, thickness of the test piece.

Figure 1A:
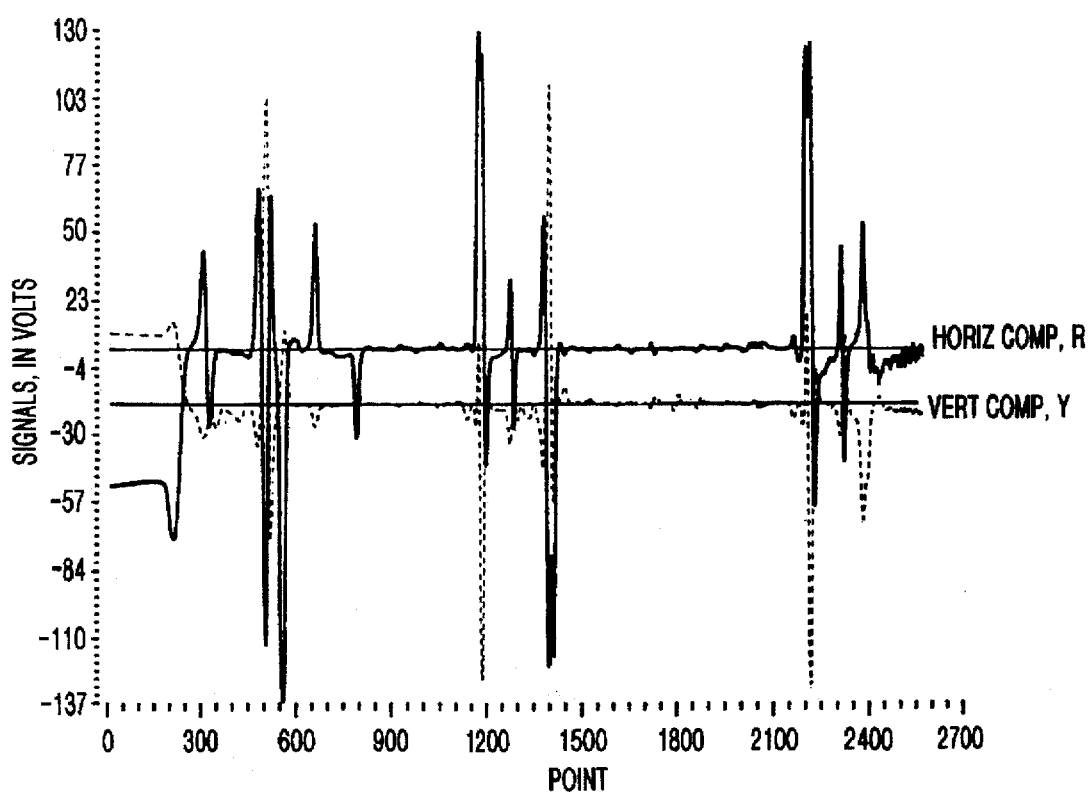
Figure 1B:
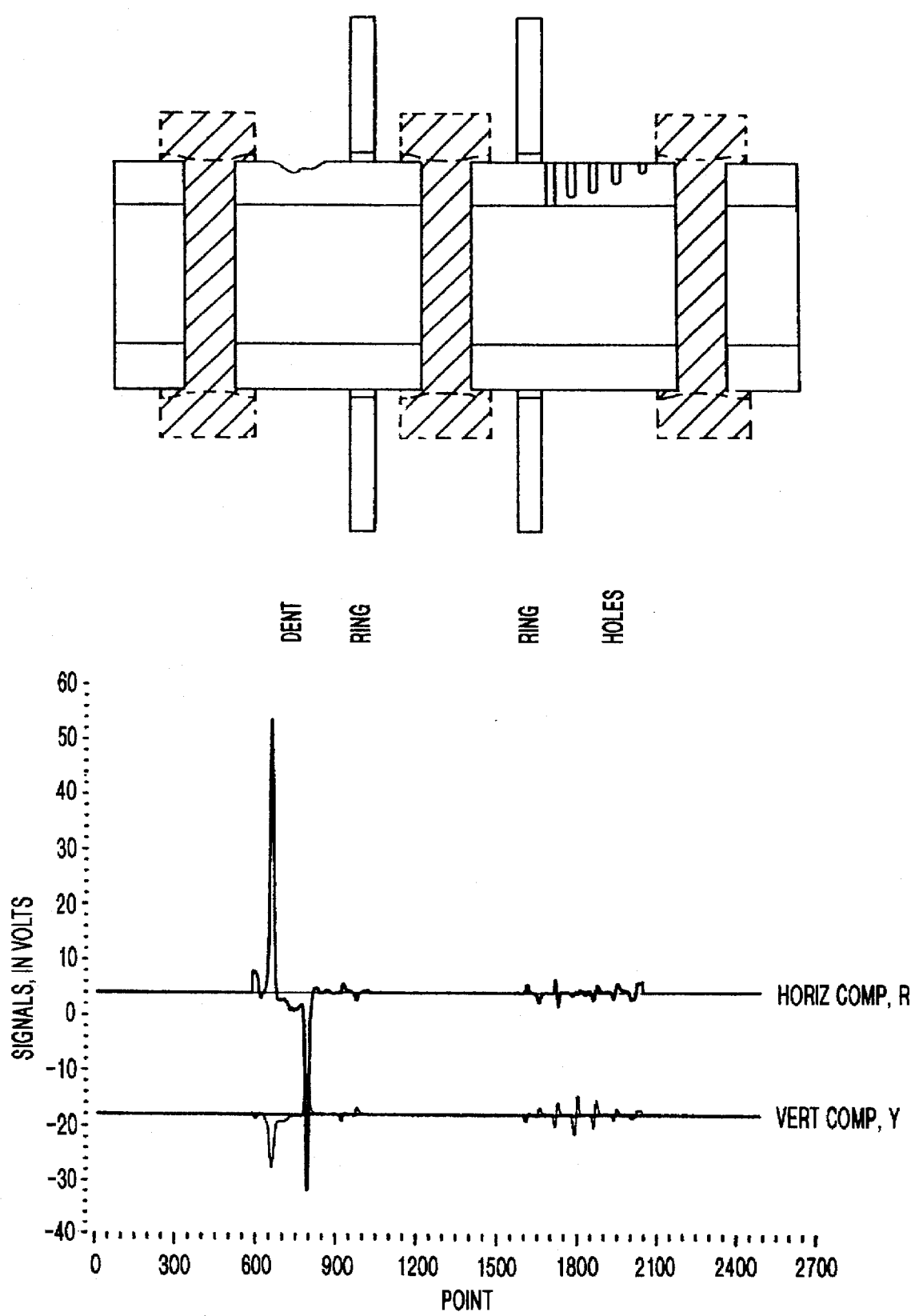
FIG. 1(b) shows the same signals after the high amplitude noise (from the connectors) has been removed.
Figure 6A:
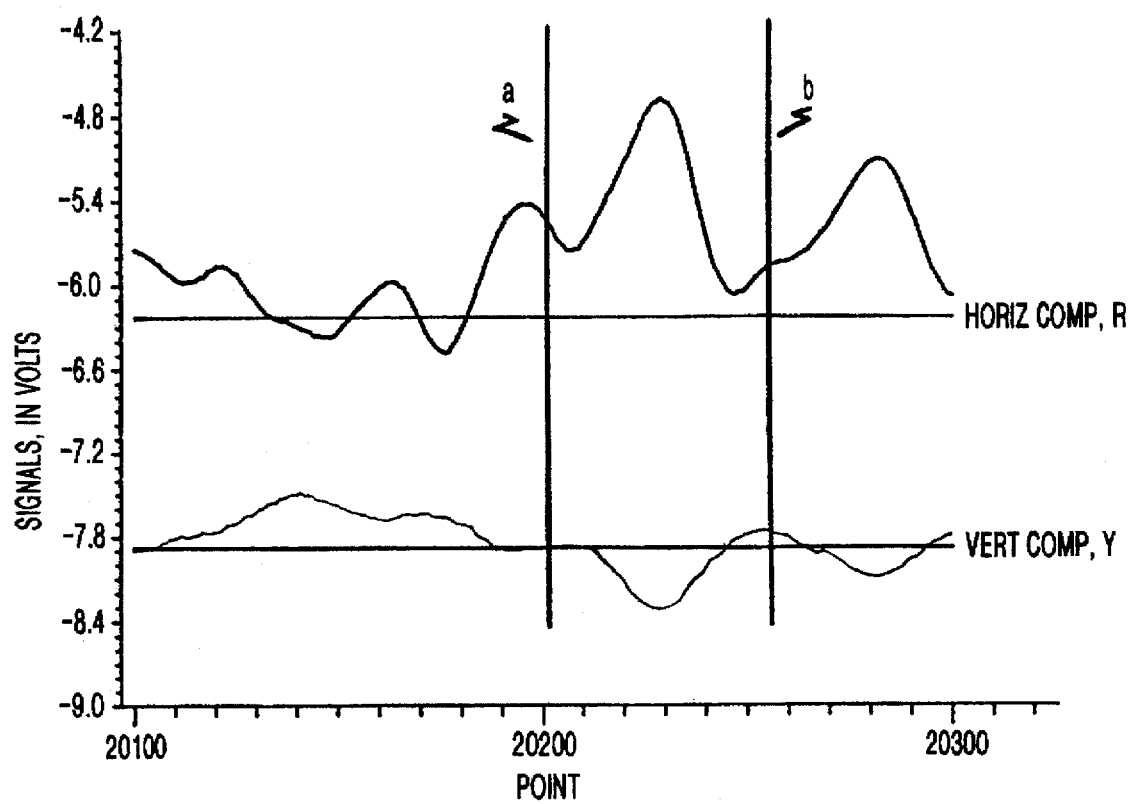
FIG. 6(a) shows a plot of the horizontal and vertical components of an eddy current signal.
Figure 6B:
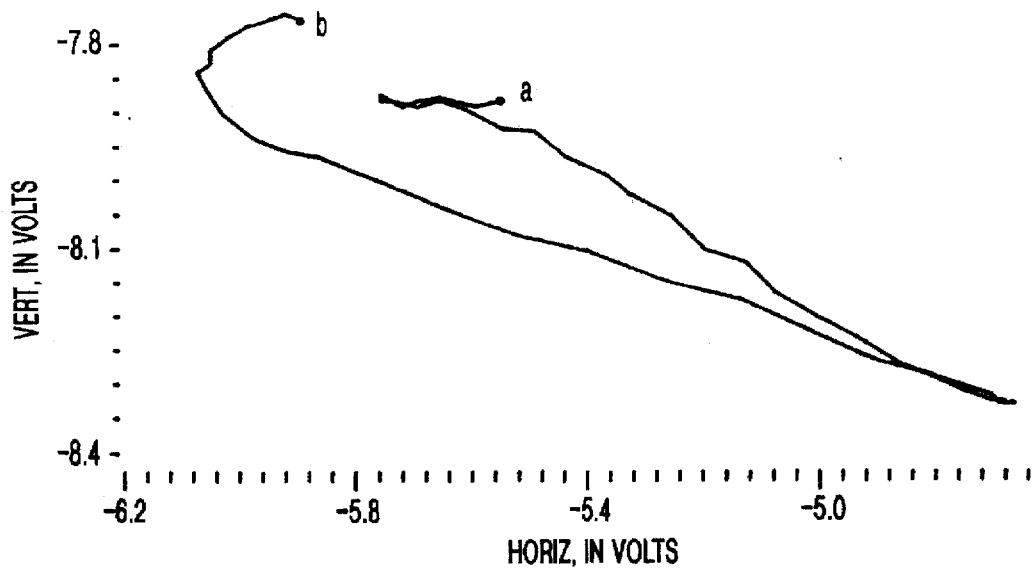
FIG. 6(b) shows a Lissajous figure constructed from the segments between the vertical fines a and b in FIG. 6(a)
Figure 7A:
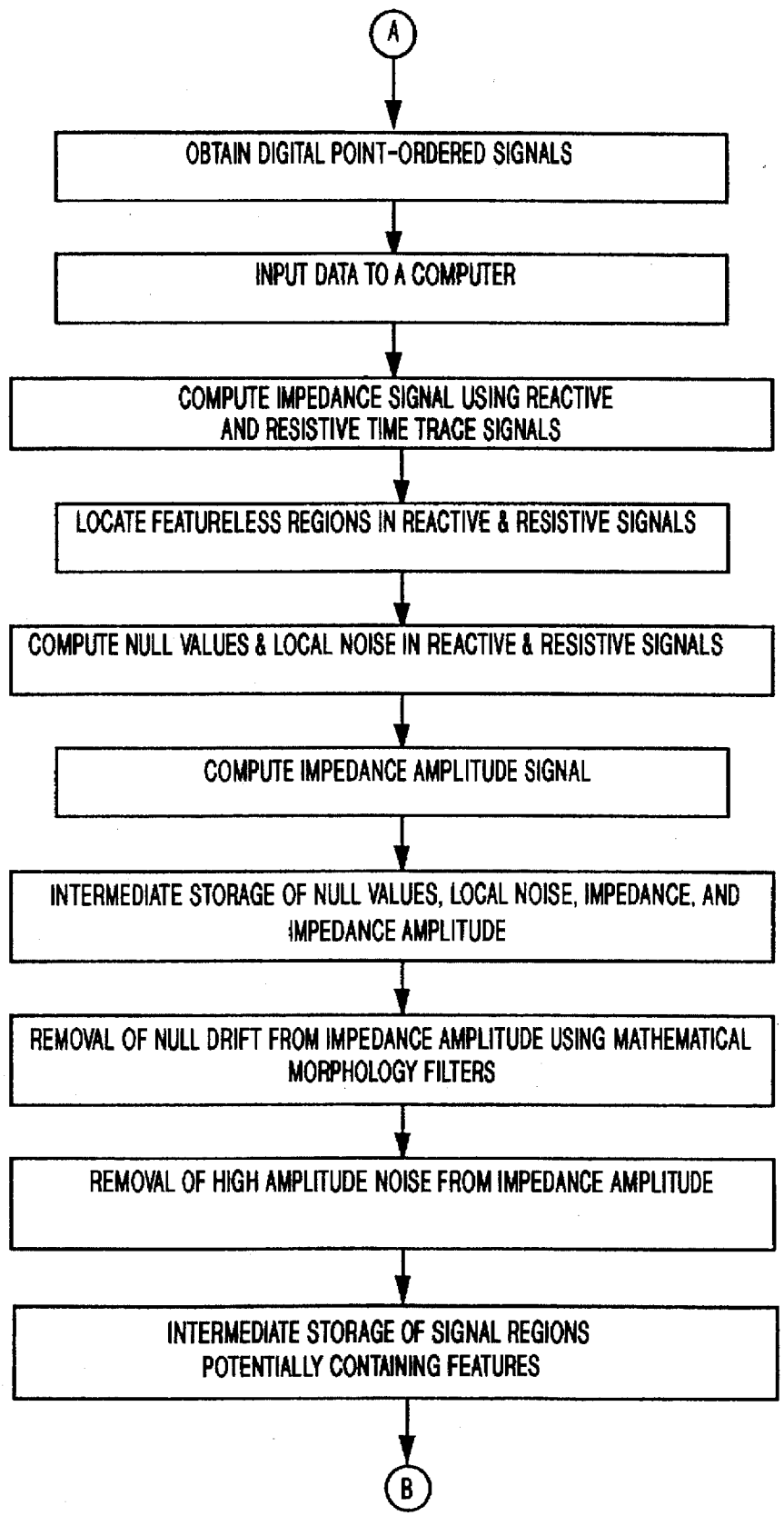
FIG. 7(a–d) is a simplified flow diagram of the method of the invention as applied to eddy current calibration signals.
Figure 7B:
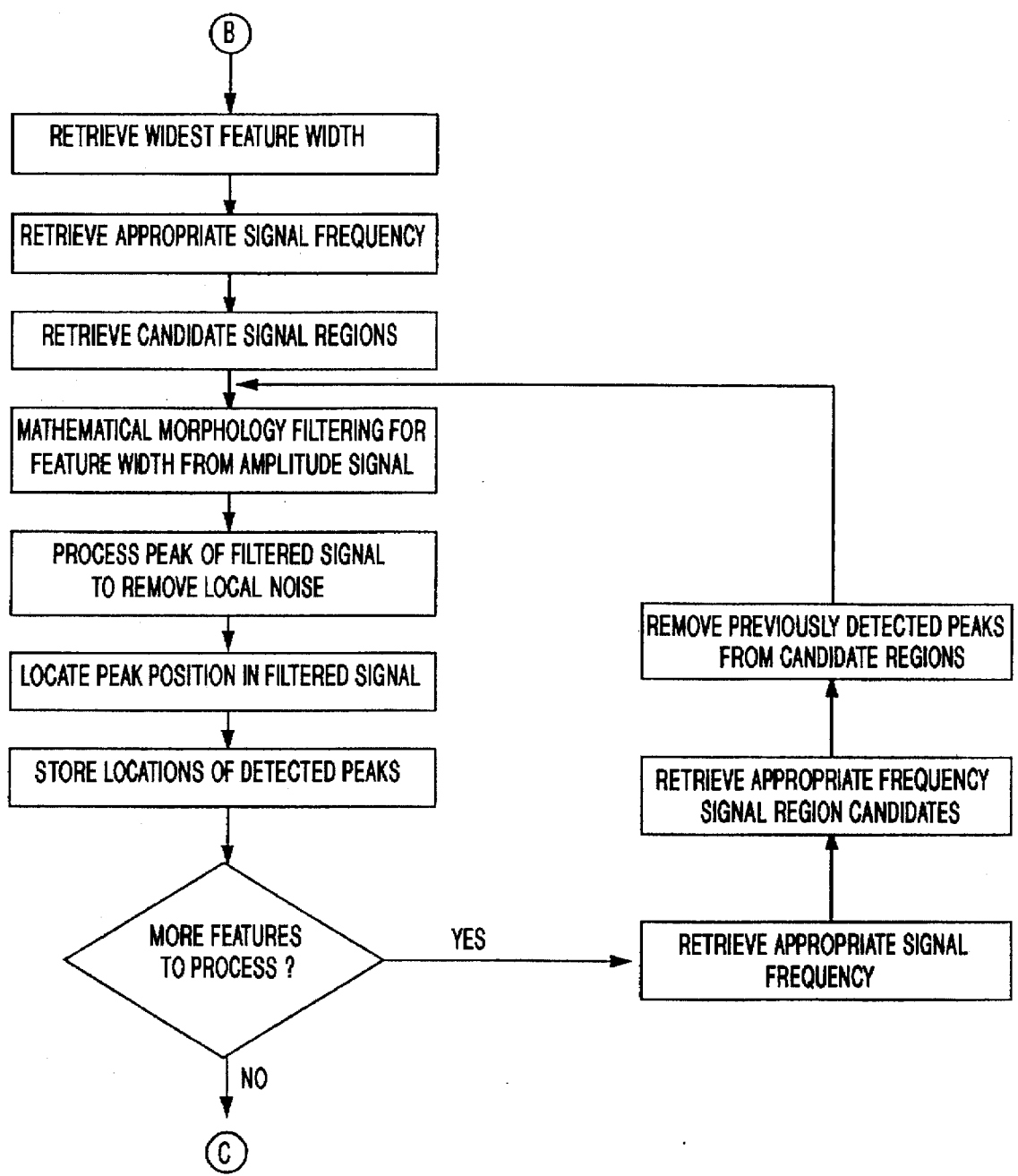
Figure 7C:
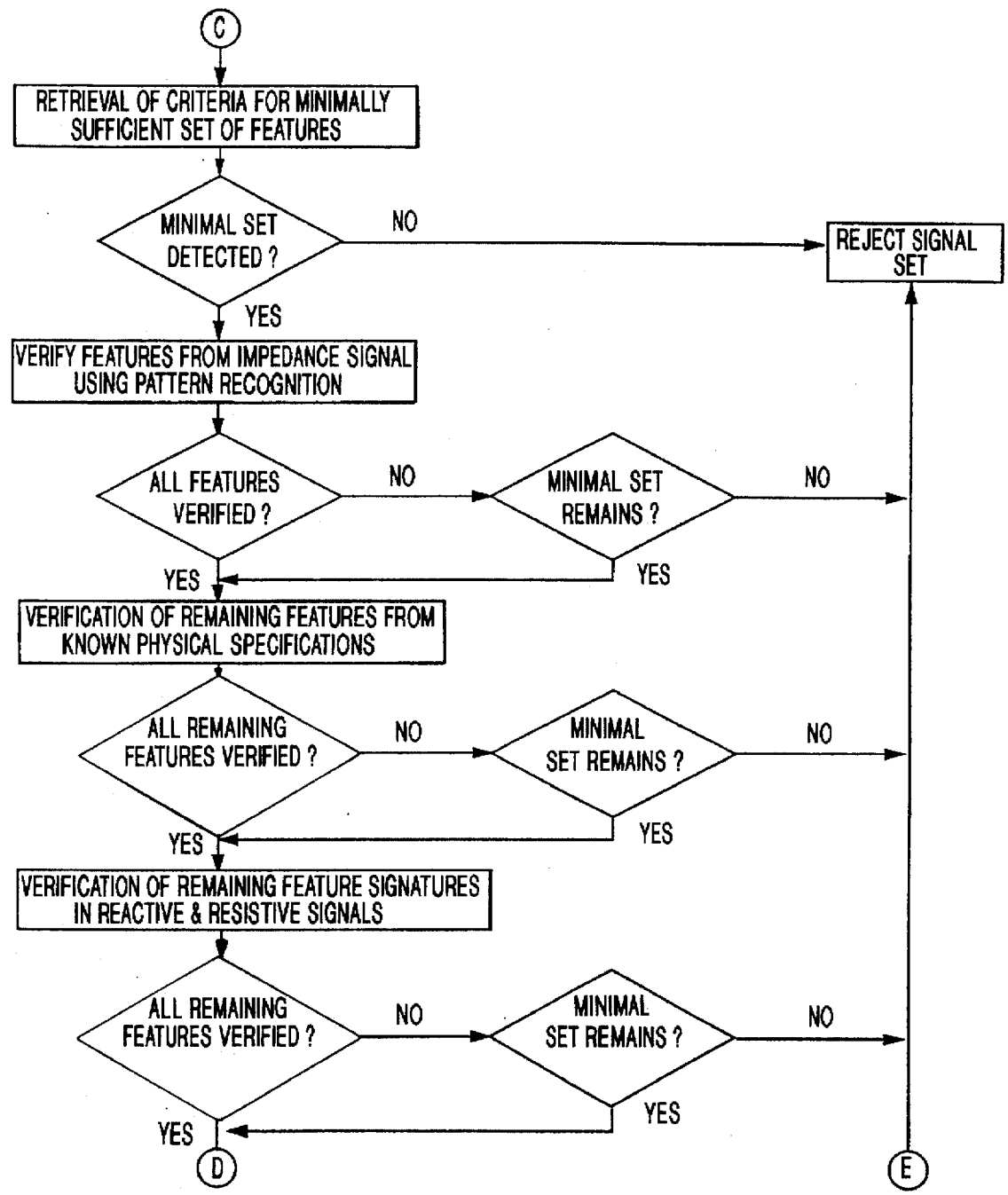
Figure 7D:
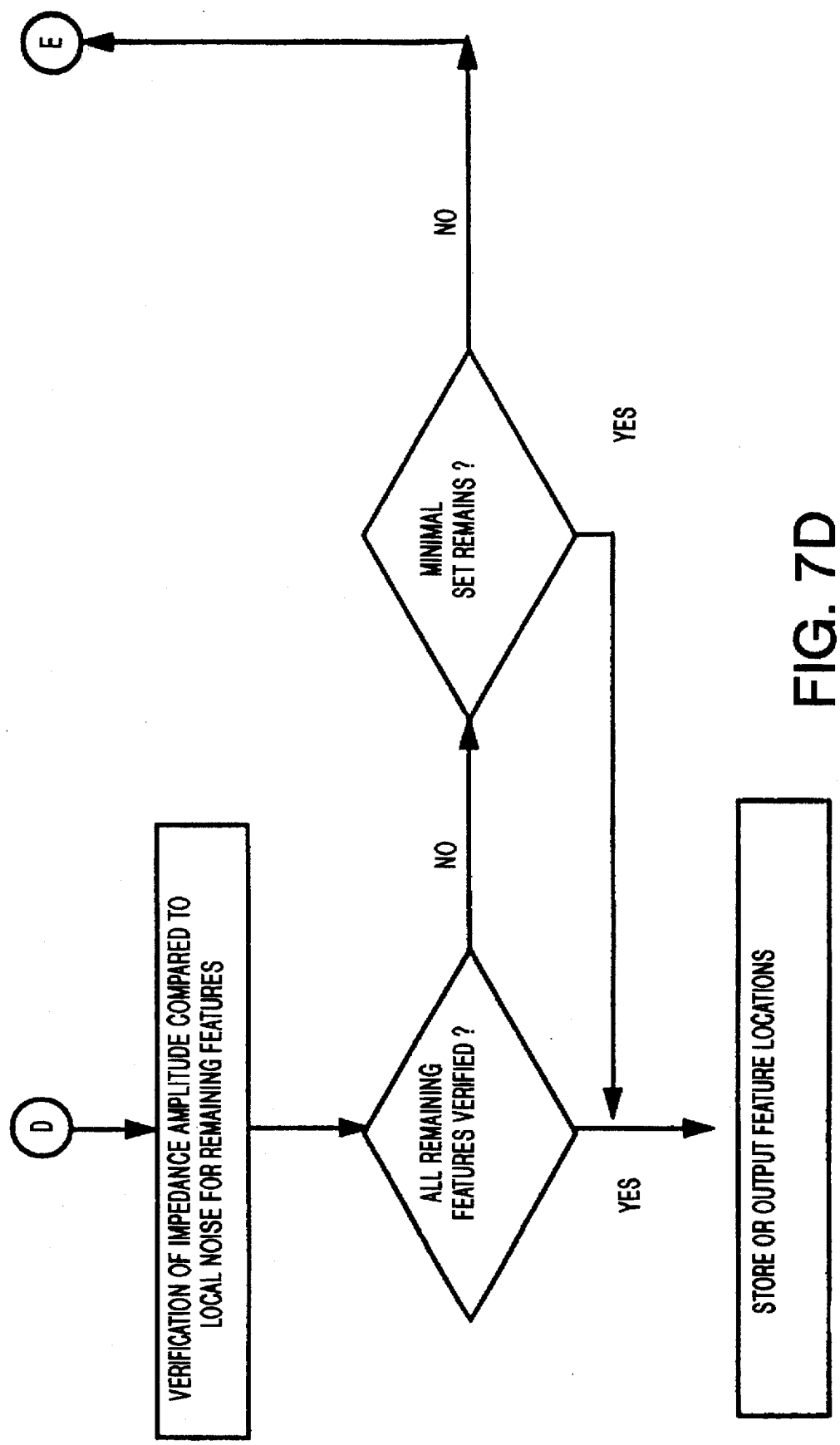

Eddy current signals may be represented in two equivalent ways, (1) as time-traces, as shown in FIGS. 1 and 2, and (2) as Lissajous patterns, as shown in FIG. 6 (b). In the time-trace view, the data is represented as two one-dimensional functions of position (or time), $$R[1,N]=\{(R_k,k), k=1,2,3,\ldots,N\}$$

$$Y[1,N]=\{(Y_k,k), k=1,2,3,\ldots,N\},$$

where R is the resistive component of impedance and Y is the reactive component of impedance. R and Y are shown together in FIG. 1(a) and separately in FIGS. 2(a) and 2(b). In the Lissajous pattern view, as can be seen in FIG. 6(b), the data are represented as one two-dimensional point-ordered signal in the impedance plane, $$Z[1,N]=\{(R_k,Y_k), k=1,2,3,\ldots,N\},$$

Where Z is the impedance signal.

Although both views contain identical information, it is often preferable to use one representation over the other for the sake of convenience or ease of calculation. In this invention, both representations are employed: the time-trace view will be used for feature location and identification purposes, and the Lissajous pattern view will be used for verification purposes.

Within a section of the test piece signal that contains no features of interest, recorded in the data from point k=k1 to point k=k2, $Z_k$ will not change appreciably within this featureless region (in the absence of noise) the time-traces, R[k1,k2] and Y[k1,k2] will be horizontal straight lines, to good approximation, since their values remain constant. The Lissajous pattern, Z[k1,k2], will be a geometric point, for the same reason. Any significant deviation from a horizontal line in the time-traces, or from a point in the two-dimensional impedance plane, indicates that some material discontinuity may be present. Deviations in the time-traces appear as peaks or dips (or both) as seen in FIGS. 1 and 2, whereas deviations in the impedance plane appear as figures resembling FIG. 8's or figure V's (or sometimes more complicated two-dimensional shapes), as shown in FIG. 6(b).

In this invention, the time-trace function used is the impedance amplitude signal A, where $$A[1,N]=\{\sqrt{[(R_k-R_0)^2+(Y_k-Y_0)^2]}, k=1,2,\ldots,N\},$$

rather than the individual components. Here $(R_0,Y_0)$ are the "null values" of impedance, i.e., the value of Z in featureless regions. The advantages of choosing A[1,N] rather than the pair, R[1,N] and Y[1,N], are as follows. For a signal feature of sufficiently large amplitude, the value of one component can be very small while the other component is appreciable;

therefore, choosing only one component for computation can lead to missed feature locations. On the other hand, choosing both components separately leads to double the computations necessary. The Choice of A[1,N] provides a much smaller calculational effort without losing relevant information.

Figure 2A:
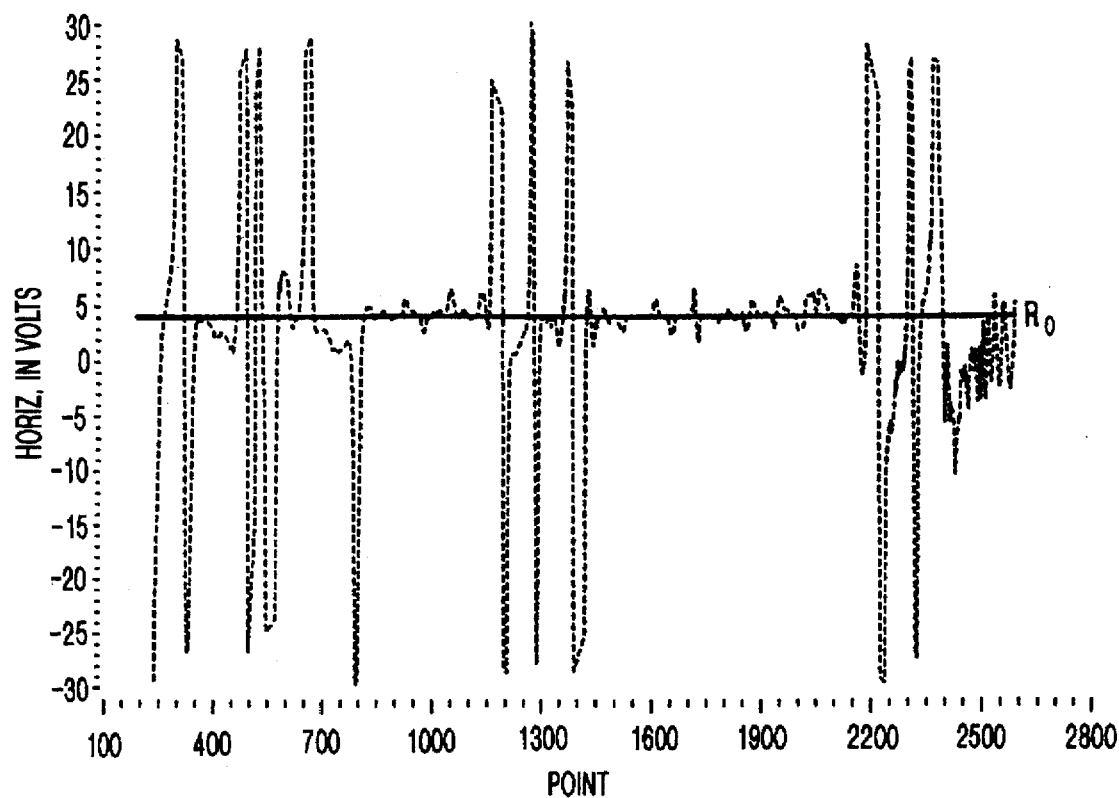
FIGS. 2(a) and 2(b) show a plot of the horizontal and vertical components of the signal in 1(a), and the computed null values $R_0$ and $Y_0$.
Figure 2B:
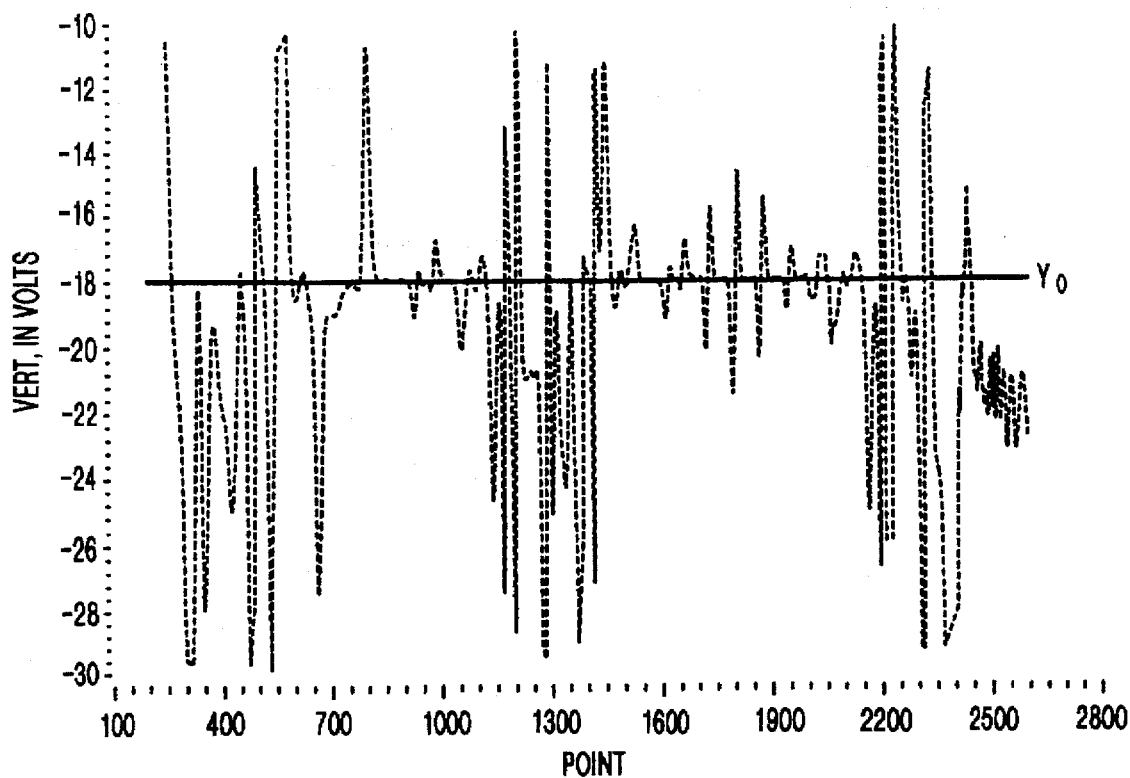

In order to compute A[1,N], the null values, $(R_0,Y_0)$, must be accurately calculated. In some cases, signals include regions of high amplitude noise along with regions of small amplitude noise, so that $(R_0,Y_0)$ cannot be computed as simple arithmetic means. In tubing inspections high amplitude noise results from the joints connecting calibration pieces, as seen in FIG. 1(a), whereas small amplitude noise results from electronic equipment fluctuations. In this invention, null values are computed by the following method. Intervals (of a given minimal length) are identified over which both the values of R[1,N] and Y[1,N] do not change appreciably. Values of R within all of these intervals are compared and those intervals with R-values significantly different from those in the majority of intervals (the "outliers") are removed; similarly for Y. What remains are the null values, $R_0$ and $Y_0$. FIGS. 2(a) and (b) show the computation of $R_0$ and $Y_0$ using the above method. All signal intervals used to compute $R_0$ and $Y_0$ are used also to compute noise level. Over these intervals, variances and covariances are computed. These statistical quantities are a measure of the noise level for that test piece.

Figure 3:
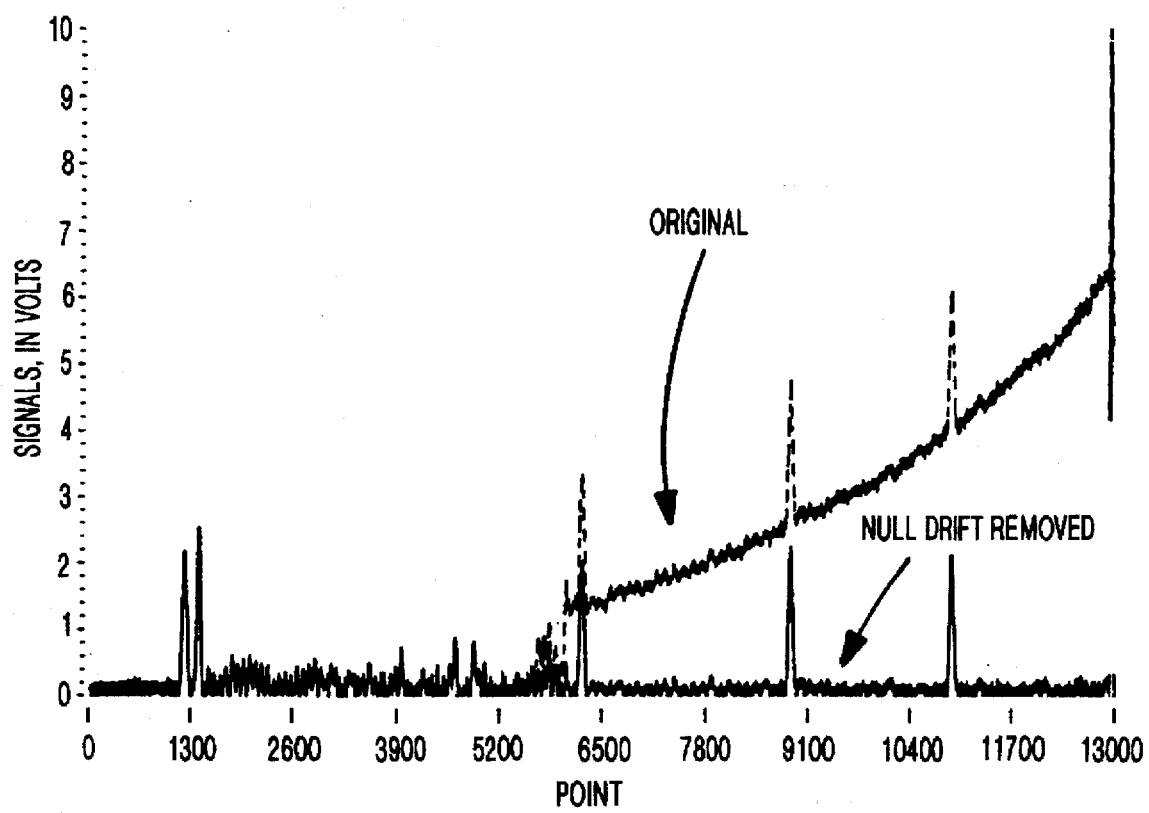
FIG. 3 is a plot of an original signal and the same signal after the null drift has been removed.

Occasionally a data set will manifest "null drifting", i.e., the null value will continuously change during measurement because of electrical drifting in the equipment and/or mechanical wearing of the eddy current probe. In order to remove null drifting, morphological filtering is imposed on A[1,N]. (If no drifting occurs, the filtering operation will not significantly change A[1,N].) This operation, called a "tophat" transformation, is performed using a linear filter of length no smaller than the width of the widest signal peak of interest. The filtered signal, A[1,N]—using the same expression to describe a signal after filtering as before filtering—will have a null baseline at 0 (Zero) amplitude, with peaks protruding from the baseline at feature locations or within regions of high amplitude noise. FIG. 3 shows null drifting removal. As illustrated in this figure, the processed signal is not distorted in any way after tophat filtering. Note that the null drift removal method is not restricted to the impedance amplitude signal; it is applicable for any point-ordered digital signal.

The final pre-processing step involves identifying and removing the high amplitude noise intervals (in this embodiment, high amplitude noise is located and removed from the impedance amplitude signal), or equivalently, identifying intervals in which features of interest can appear. Since the physical length of the calibration piece is known in advance, the segments of signal containing features of interest satisfy the two criteria:

a) the number of data points in a segment must closely correspond to the length of the piece times the (known) measurement speed, and b) the amplitude everywhere in a segment does not exceed a given threshold. The signal amplitude is divided into three regions—low amplitude noise, feature amplitude, and high amplitude noise. The amplitude level that divides the feature amplitude and high amplitude noise is chosen for the threshold. In this embodiment, a broad survey of historical data was used to establish the threshold.

Measurement speed, mentioned in (a) above, is given in units of (number of pts./length), which is the recording frequency (number of pts./sec.) divided by the probe speed, given in units of (length/sec;). in ET measurements the probe speed is held constant, at least over distances of typical feature size. All segments not obeying both of the above criteria are noise segments and are removed; all other segments are candidates for further investigation. See FIG. 1(b). These criteria are sufficient for identifying/removing high amplitude noise regions of the signals because the possibility of null drifting has been eliminated.

For the preferred embodiment, using eddy current signals, the reactive and resistive time trace signals have been used to compute an impedance amplitude. This impedance signal is then used to find the features of interest. However, for other applications, the method steps of the invention could be applied to any digital point-ordered signal of interest to detect known features.

C. Feature Detection

Upon completion of the signal pre-processing step, a detection process is used to locate signal features for further evaluation. In the case of tubing inspection calibration, several different types of signal features need to be located, such as those produced by drilled holes of various depths, by externally attached rings, and by dents.

The method of detection is based on isolating signal peaks using peak width filters of progressively smaller size. Choice of filter size is governed by the known lengths of the features to be detected. This method does not apply learning algorithms to previously identified features. Therefore, the system does not require information from prior analyses or a pre-test learning phase. In addition, detection capability is optimized by utilizing the known depths of features of interest. Length and depth information are exploited in the following manner.

Length

The width of a signal peak is a direct measure of the (known) length of a test feature, since the speed of the probe is held constant during the measurement process. Here feature length refers to the dimension in the direction of probe motion. Different features have different lengths, so that signal peak widths may be used to differentiate between features. For example, the calibration piece used in tube inspections can contain drilled holes as well as externally mounted rings. Holes simulate defects and external rings simulate support structures. The diameters of the holes are typically much smaller than the thickness of the external rings; thus the signal peaks of the latter are wider than those of the former.

Depth

Depth information is obtained by use of the appropriate frequency signal. For example, for tube inspections, peaks produced by support ring(s) will be most prominent in the lowest frequency signal (corresponding to the probed distance furthest from the electromagnetic coils), whereas the peaks produced by drilled holes will be most prominent in a higher frequency signal.

1. Isolating the widest signal peaks

Starting with the pre-processed signal at the frequency appropriate to the longest feature (widest peak—for tube calibrations this will be the lowest frequency signal), all non-noise intervals are interrogated in the following way. A morphological tophat filtering is performed, using a filter whose length is intermediate between the expected width of the widest peak and the expected width of the next widest peak. The result of this operation is to filter out all peaks but those due to the feature with the widest peak.

2. Locating the peaks

Figure 4A:
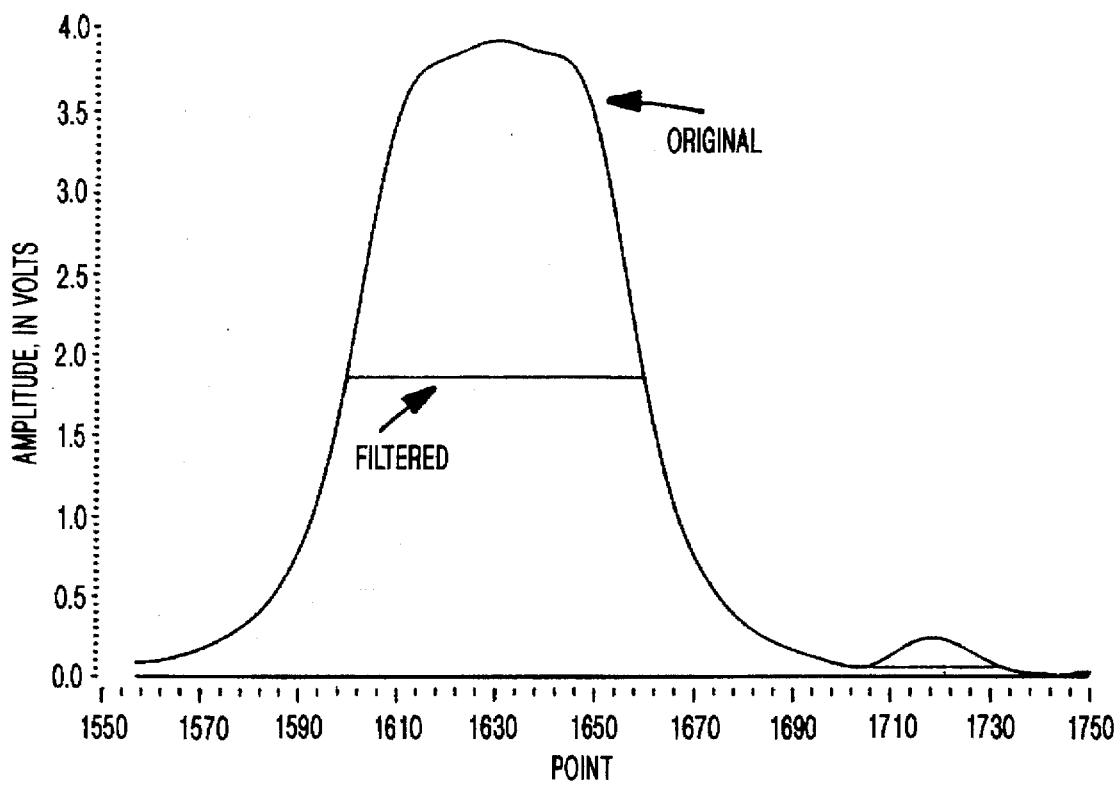
FIG. 4(a) shows the shape of an original and a filtered signal.
Figure 4B:
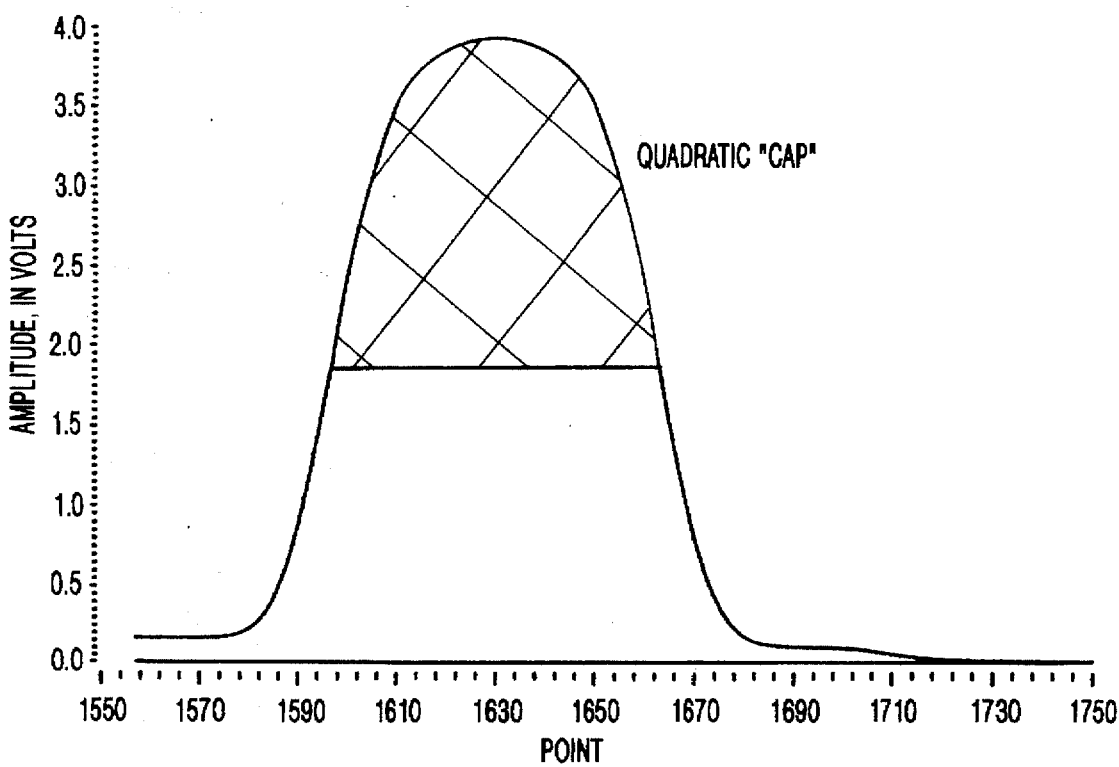
FIG. 4(b) shows the replacement of the top of the peak of the same filtered signal with a quadratic "cap" (hatched area)

The locations (peak locations and peak widths) are obtained by identifying the position on the x-axis (point) of the highest amplitude value of a peak. The validity of this criterion for peak finding assumes an approximately quadratic functional behavior for a peak, an assumption not always true. In order to guarantee quadratic behavior, an additional sequence of morphological operations is performed in which the upper portion of a peak is removed, and replaced by a quadratic "cap". This is shown in FIGS. 4(a) and (b). This type of peak replacement is a novel aspect of the method of the invention as it provides robustness to feature detection by effectively ignoring insignificant local fluctuations in the vicinity of the peak. Reliability of detection is, thus, greatly enhanced by this novel filtering process.

3. Isolating the next widest signal peaks

The next longest feature is then looked for in the frequency signal in which its peaks are most prominent. The portion, or portions, of the interval containing the longest feature previously obtained is (are) removed. The widest peak in the filtered signal now represents this next longest feature. The above detection method (steps 1 and 2) is then repeated to locate all peaks of this desired width.

This iterative method can be repeated as many times as is necessary to locate all features of interest. It is important to note that the sequencing of peaks in the signal plays no role at all in the detection method described above. Thus it is an advantage of this invention that feature detection does not depend on sequencing in the test piece. It is also important to note that all the morphological filtering operations described above will not change a signal that does not contain peaks to begin with. Therefore, the absence of peaks in the signal cannot confound the detection method of this invention. Thus it is a further advantage of this invention that feature detection does not depend on the presence or absence of any particular feature in a test run.

Figure 5A:
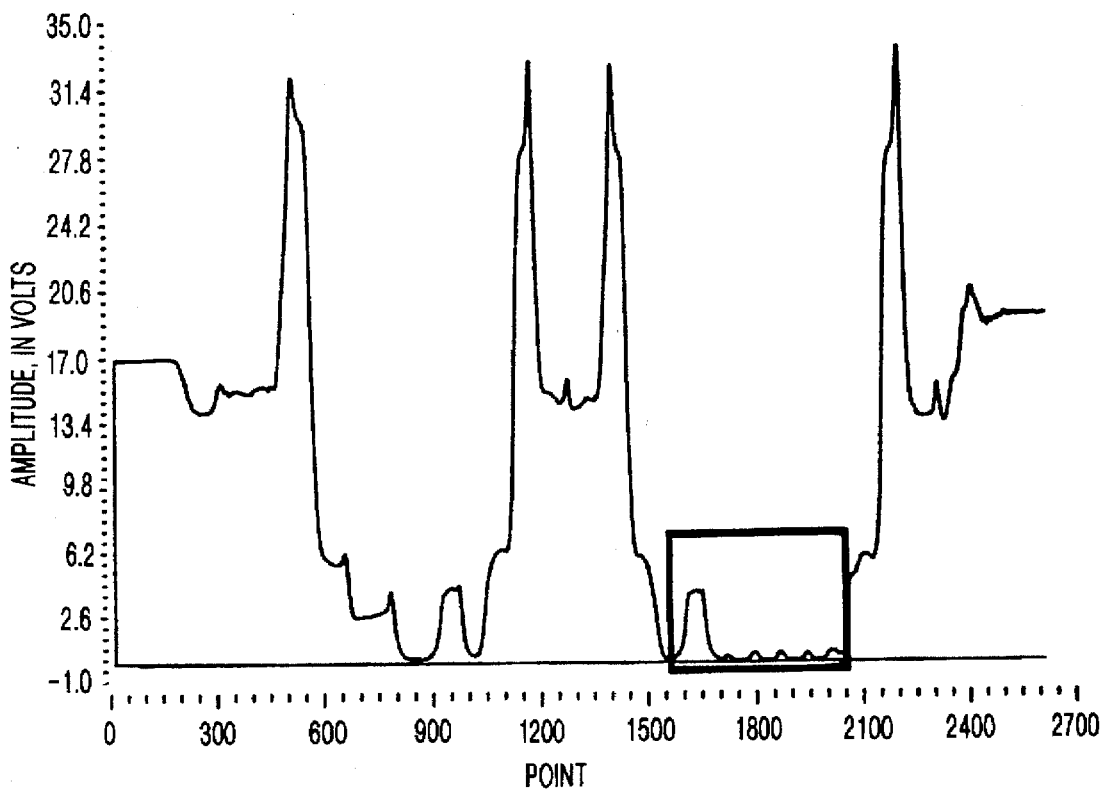
FIGS. 5(a)–(f) depict the automated feature detection process as applied to eddy current signals from a tube calibration piece.
Figure 5B:
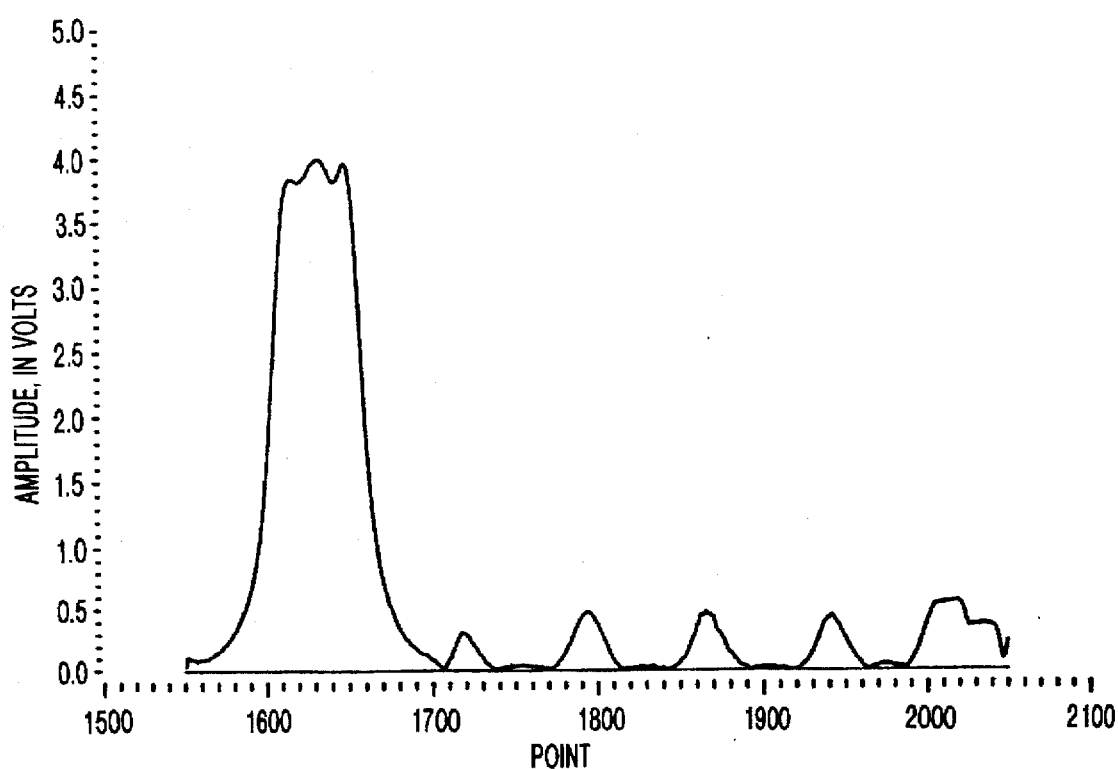
Figure 5C:
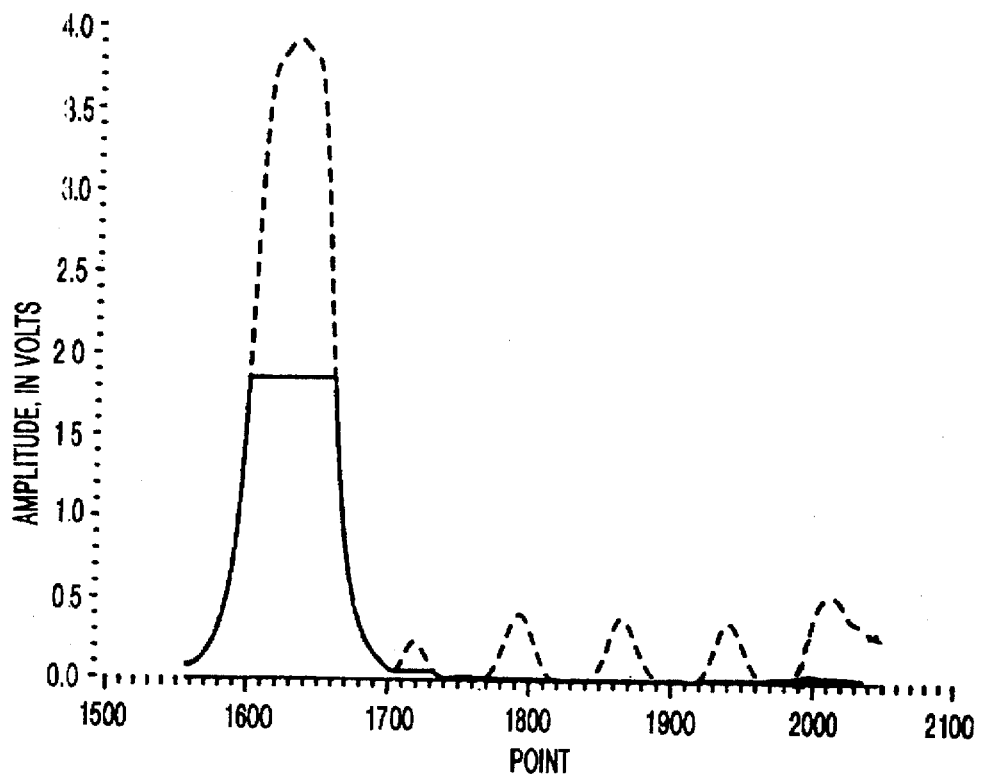
Figure 5D:
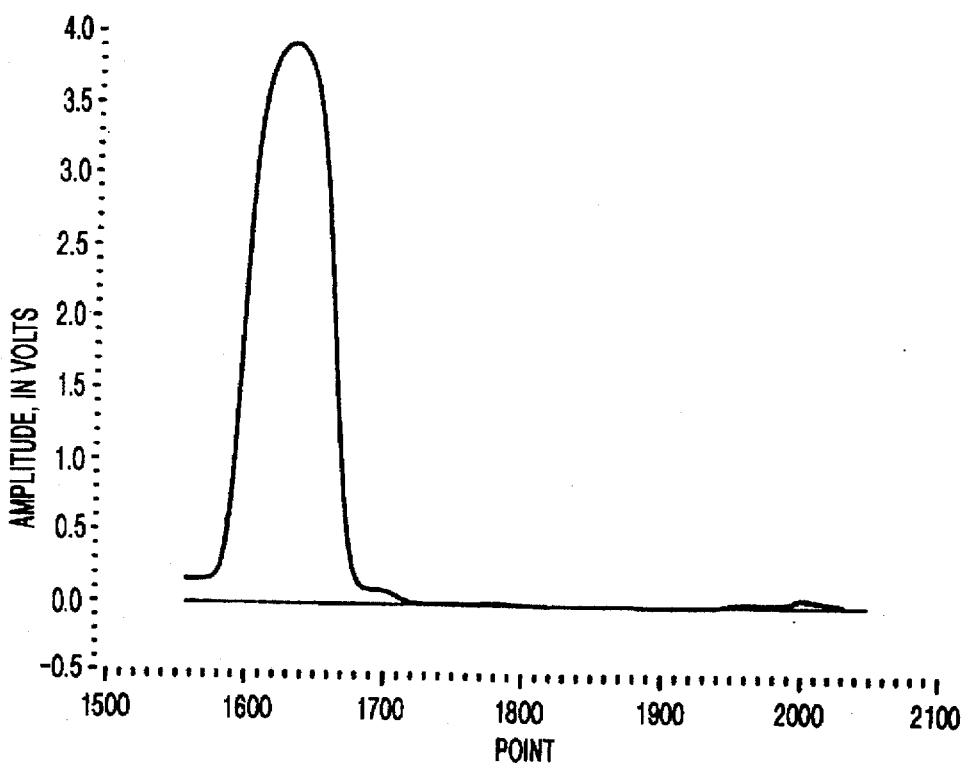
Figure 5E:
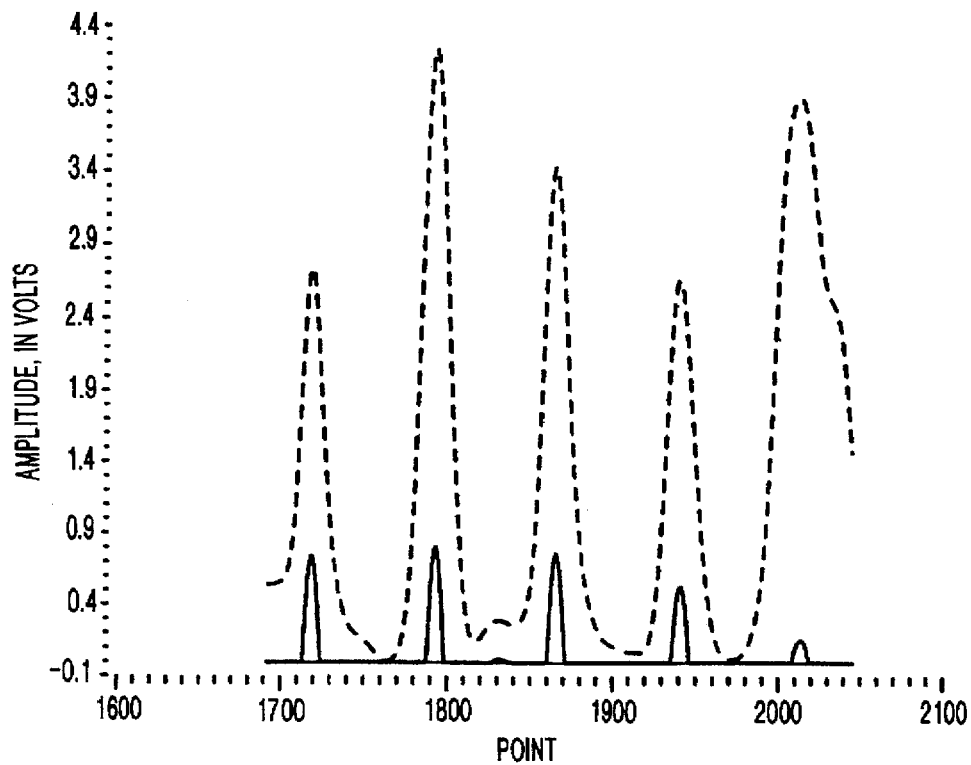
Figure 5F:
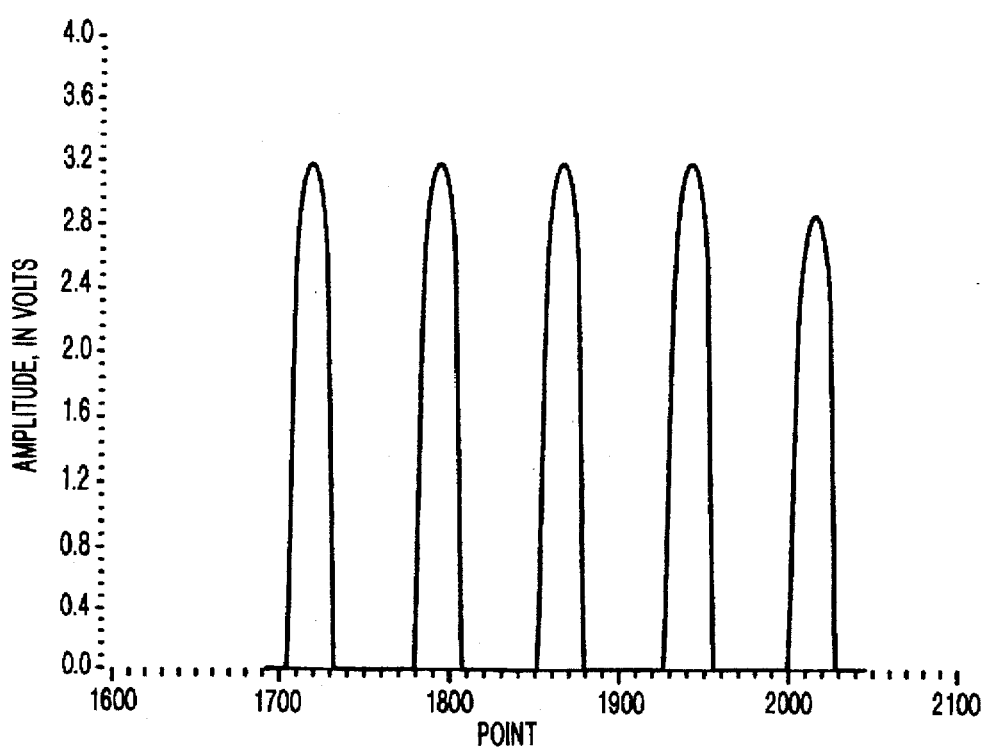

The feature detection method of the invention can best be understood by referring to FIGS. 5(a)–(f). These Figures show a preferred embodiment of the invention wherein the method is applied to an eddy current signal to detect an external ring and five drilled holes in a tube calibration piece. FIG. 5(a) shows the impedance amplitude signal A of a signal at the lowest frequency (from the same set of signals depicted in FIG. 1). A box is drawn around a non-noise segment in FIG. 5(a), and the boxed section is enlarged in FIG. 5(b). Using a filter of size less than the known size of the ring peak, but larger than the known size of the drilled holes peaks, the signal segment is transformed to that of FIG. 5(c). The top part of the ring peak and all the peaks of the holes (in dashed lines in FIG. 5(c)) are missing in the filtered signal (solid line). A quadratic "cap" then replaces the missing top portion of the ring peak, using appropriate morphological filters, as shown in FIG. 5(d). The ring peak, the only one remaining, thus is identified. FIG. 5(e) shows the same signal segment as that given in FIG. 5(b), but at a higher frequency and with the portion due to the ring cut out. The remaining signal segment contains indications due to the holes. In FIG. 5(e) the unfiltered signal is depicted (dashed lines) along with the filtered signal (solid lines). FIG. 5(f) shows the signal after further morphological filtering (and re-scaling, for purely aesthetic reasons) has taken place.

The table below lists the tabular results of the entire detection process for this calibration run showing the feature detected (external rings, holes,, and dents), and the beginning and end sequential point locations of the identified feature.

TABLE

Calibration Results

| Feature | Point Number | |
|---|---|---|
| | Start | End |
| Support Ring #1 | [ 886, | 993] |
| Support Ring #2 | [1577, | 1686] |
| 1st ASME Hole | [1708, | 1742] |
| 2nd ASME Hole | [1778, | 1817] |
| 3rd ASME Hole | [1854, | 1890] |
| 4th ASME Hole | [1931, | 1966] |
| 5th ASME Hole | [1997, | 2050] |
| Profilometry Standard | [ 587, | 817] |

D. Verification methods

Since incorrect identification of calibration features can lead to serious diagnostic errors, it is important to require the highest possible assurance for calibration feature identification. This implies the capability of disqualifying a calibration run if certain requirements are not met. It is an important feature of the automated process of the invention to be able to make such a judgment.

The methods of verification/disqualification in this invention are based on pattern recognition techniques together with inherent properties of eddy current behavior. They make use of the Lissajous representation of eddy current signals, in addition to general information concerning the physical layout, or physical characteristics, of calibration standards. Another important feature of the invention is that the detection and verification methods are independent.

A minimum set of features must be present in order to properly calibrate an eddy current system. The nature of the minimum set can be defined differently for different applications. For example, in tubing calibration, one external support ring and a series of five drilled holes are required for calibration. Other features, while not necessary, provide useful information for signal analysis. For example, additional support rings, or dent (known in the art as a profilometry standard) can appear in a tube calibration standard. Information from these signal features can be used to construct a hybrid set of signals, called "mixed signals" in the art, that provide additional verification for identifying indicated signal features.

Described below are four methods of the invention used to verify the detected identity and location, of the known features. It is not necessary to use all four, although all four are used in the preferred embodiment. The order of use is not important.

1. Verification from Lissajous shapes

The various calibration features can be distinguished by geometric parameters obtained from characteristic Lissajous patterns. Both the pattern class (e.g. FIG. 8 or figure V's) and the quantitative evaluation of the parameters are determined by automated pattern recognition methods, using an expert system, that operate on the relevant eddy current signals. In this manner, this invention emulates human analysts who verify features by visually inspecting the Lissajous patterns produced by the signals. The automated pattern recognition methods are based on Gaussian filtering techniques, as described in "Expert System for Analyzing Eddy Current Measurements", U.S. Pat. No. 5,339,256, issued Aug. 16, 1994, incorporated herein by reference. The geometric parameters are chosen from fundamental eddy current quantities that are known to discriminate the various types of calibration features. For example, a figure-8 Lissajous pattern formed by a support ring will have lobes significantly wider than those formed by a drilled hole. Relative width, then, is one discriminating verification quantity. All parameters used for confirmation purposes are obtained only from within each set of calibration signals, i.e., no matching of parameters from previously-analyzed sets is performed. The automation of the technique using only inherent geometric parameters, derived from the corresponding Lissajous shape, in order to verify eddy current features is another novel aspect of this invention.

2. Verification from physical layout

Calibration features can also be verified using inherent information concerning the physical layout, or physical characteristics, in the calibration pieces, The time-trace representation, as well as the Lissajous representation, can be used. In tubing inspection, for example, an ASME (American Society of Mechanical Engineers) standard containing five drilled holes with known inter-hole spacing, is a part of the calibration standard. In this case, this invention can use measurements made in the time-trace representation to verify that there are five detected peaks with the correct inter-hole spacing; these peaks are tentatively identified as representing drilled holes, and verified using pattern recognition methods on the corresponding Lissajous patterns. If less than five signal peaks are detected, or if the pattern for one of the five holes produces a geometric parameter that falls outside defined limits, then the run is disqualified.

3. Verification from signature information

An additional check of features is provided by assuring that peaks detected in the impedance amplitude have the correct signatures in the impedance time-trace signals. For example, a drilled hole will, have a dip followed by a peak in the time-trace signal. This aspect of the invention can also be viewed as an independent detection method for certain calibration features, but whose results must be consistent with the feature detection methods described in Section. C in order to confirm the calibration run. Should the feature detection methods of Section C fail for a particular set of calibration signal features this signature information method can serve as the only detection method for locating these features. The other verification tests will still be applied to the results in order to confirm/reject.

4. Adaptive peak determination method

A further independent test is made to assure that the peaks found in the time-traces are significantly distinct from the small amplitude noise in the vicinities of the calibration features. This test is done by comparing the amplitudes of signal noise in a featureless region with those of the detected calibration features. This method does not rely on an a priori definition of the noise level, but rather adapts automatically to the inherent noise level in any given eddy current inspection. This adaptive peak technique is a novel feature of this invention.

When the demanded level for accepting a calibration signal set is stringent, then the expected reliability of feature detection is enhanced. At the same time, the expected rejection rate of calibration runs will also be great. If the rejection rate should be too great for a given application, then the verification requirements can be relaxed. The flexibility of adjusting the rigor of the verification criteria is another important aspect of this invention.

The preferred embodiment of the invention described above is outlined in the flow chart shown in FIG. 7(a)–(d). In the preferred embodiment, after the features of an eddy current calibration standard have been located and identified, the location and identity data can then be used to carry out the calibration of an eddy current system. For example, the calibration data can be input to a computer and used for calibration in a system such as the expert system disclosed in U.S. Pat. No. 5,339,256.

While the present invention has been described with respect to an exemplary embodiment thereof, it will be understood by those of ordinary skill in the art that variations and modifications can be effected within the scope and spirit of the invention. The method of the invention is not limited to eddy current calibration signals but can be used, for example, with ultrasonic, acoustic, or any other signals produced by any instrument; which are digital point-ordered signals, wherein all features which might be present are known in advance.

We claim:

1. A computer implemented information-extraction method that locates and identifies features in digital point-ordered signals, said signals representing data from test material containing one or more known physical features, wherein said method is independent of the number and position of said features, comprising the steps of:

(a) obtaining data from said test material in the form of digital point-ordered signals;

(b) inputting said digital point-ordered signals into a computer;

(c) processing said digital point-ordered signals to remove noise;

wherein said processing includes determining the null values of said signals independent of irrelevant signal features including regions of high amplitude noise, removing long-term signal trends, including null drifting, by morphological filtering of said signals, and locating and removing noise regions of high signal amplitude in said signals;

(d) detecting features of said signals, representing known features of said test material, using a computer assisted morphological filtering process to locate positions of peaks of said signal features using peak width filters of progressively smaller size;

(e) verifying any features detected in said signals using a computer implemented expert system of signal pattern recognition and applying geometric criteria; and (f) outputting information about the identity and location of any detected known features of said test material.

2. The method of claim 1 further comprising selecting peak width filter size based on known geometrical properties of features in said test materials.

3. The method of claim 2 wherein said step (d) further comprises using a computer assisted method for assuring quadratic behavior of said peaks comprising applying a morphological operation to replace the top portion of said peaks with a top that exhibits pure quadratic behavior.

4. The method of claim 3 wherein said computer implemented signal pattern recognition further comprises measuring geometric parameters from Lissajous patterns of said signals.

5. The method of claim 3 wherein step (e) further comprises comparing information known about the physical properties or physical layout of said known features of said test material with the features detected in steps (a)–(d).

6. The method of claim 3 wherein, step (e) further comprises comparing the peaks detected in the signal amplitude for a particular feature with corresponding peaks in a time-trace signal.

7. The method of claim 3, comprising verifying said detected features by comparing the amplitudes of signal noise in a featureless region of time-trace plots with amplitudes of features detected in steps (a)–(d). wherein said method adapts automatically to an inherent noise level in each set of said signals.

8. The method of claim 1 including rejecting any one signal or set of said signals which does not contain a prespecified minimum number of features.

9. The method of claim 8 wherein said prespecified minimum number of features is adjustable for a given application.

10. The computer assisted automated information-extraction method of claim 1 wherein said digital point-ordered signals are eddy current calibration signals.

11. A computer assisted system for automatically locating and identifying features in digital point-ordered signals, said signals representing data from test material having known physical features, comprising:

means for generating digital point-ordered signals from said test material;

means for acquiring signal data representing said signals generated;

means for inputting said signal data to a computer;

means for processing said signal data to remove noise; wherein said means for processing includes means for computing the null values of said signal data, means for removing null drifting, and means for computing an amplitude signal;

means for detecting of said signal data, using mathematical morphology filter means comprising means for locating signal peaks using peak width filters of progressively smaller size, wherein said features of said signal data represent known physical features of said test material;

means for verifying any features detected in said signals by applying a computer implemented expert system of signal pattern recognition and geometric criteria application; and means for outputting the identity and location of any detected know features of said test material.

12. The system of claim 11 wherein said means for detecting further comprises means for assuring quadratic behavior of said signal peaks.

13. The system of claim 12 wherein said means for verifying comprises computer assisted means for determining inherent geometric parameters from said signal patterns.

14. The system of claim 12 wherein said means for verifying comprises means for comparing impedance amplitude to impedance time-trace signals of said digital point-ordered signals.

15. The system of claim 12 wherein said means for verifying comprises means for comparing amplitudes of signal noise in a featureless region of said digital point-ordered signal with amplitudes of features detected in said signals.

16. The system of claim 11 further comprising means for inputting and applying minimal rejection criteria for rejecting any one signal or set of signals when a prespecified number of said known features is not found, and means for adjusting said criteria.

17. A computer-based method for automatically locating and identifying features in digital point-ordered signals, said features representing physical features of an eddy current calibration standard, comprising:

(a) generating digital point-ordered signals by applying an eddy current probe to a calibration standard containing known physical features;

(b) receiving said signals from said standard at several frequencies;

(c) inputting said signals into a computer;

(d) computing, an impedance signal at each of said several frequencies;

(e) computing null values of said digital point-ordered signals from the resistive and reactive components of time-trace impedance signals;

(f) computing an impedance amplitude signal for each said frequency;

(g) processing each said impedance amplitude signal to remove noise and null drifting;

(h) selecting an impedance amplitude signal from step (g) for the frequency appropriate to the longest physical feature;

(i) isolating signal peaks in said impedance amplitude signal by an iterative method using peak width filters of progressively smaller size;

(j) applying a morphological filtering process to said peaks to assure quadratic behavior;

(k) identifying the location on the x-axis of peaks having the highest amplitude value;

(l) selecting the impedance amplitude signal for the frequency appropriate for the next longest physical feature;

(m) removing peaks found, for any feature previously identified, from the signal selected in step (l);

(n) applying the process of steps (i) through (m) to said signals at other frequencies;

(o) verifying features detected, and outputting locations and identities of said detected features.

18. The method of claim 17 wherein said step of verifying comprises determining inherent geometric parameters of said impedance signal using an expert system of signal pattern recognition.

19. The method of claim 17 wherein said step of verifying comprises applying inherent information about the physical layout of said features in said standard.

20. The method of claim 17 wherein said step of verifying comprises comparing the peaks detected for a feature in the impedance amplitude signal with the known signature of said feature in a time-trace signal plot.

21. The method of claim 17 wherein said step of verifying comprises comparing amplitudes of signal noise in a featureless region of a time-trace signal with the amplitude of said detected feature, wherein said method adapts automatically to an inherent noise level in said signals.

22. The method of claim 17 further comprising setting minimal rejection criteria, and rejecting any one signal feature or set of signal features that does not meet said criteria.

23. The method of claim 17 further comprising providing said identities and locations of detected calibration features to an eddy current system to calibrate said system.

* * * * *

UNITED STATES PATENT AND TRADEMARK OFFICE
CERTIFICATE OF CORRECTION

PATENT NO. : 5,737,445

DATED : April 7, 1998

INVENTOR(S) : Jane L. Oppenlander, Kent C. Loomis, David M. Brudnoy and Arthur J. Levy It is certified that error appears in the above-identified patent and that said Letters Patent is hereby corrected as shown below:

In column 1, line 7, after "further" add a comma -- , --.

In column 1, line 9, delete the comma after "signals".

In column 2, line 22, add a comma -- , -- after "e.g.".

In column 4, line 29, delete "one" and insert therefor -- a --

In column 4, line 55, change "FIG. 8's or figure V's" to -- figure-8's or figure-V's -- .

In column 5, line 33, change "A[1,N]. (If" to -- A[1,N] (if --.

In column 5, line 34, change "A[1,N].)" to -- A[1,N]). --.

In column 6, line 36, insert a comma -- , -- after "Here".

In column 7, lines 64 and 66, "feature" to -- features -- .

In column 8, line 39, delete the comma "," after the word "rings", change "dent" to -- dents -- , and delete "a".

In column 8, line 40, change "standard" (2nd occurrence) to --standards--

In column 8, line 43, change "provide" to -- provides --.

UNITED STATES PATENT AND TRADEMARK OFFICE
CERTIFICATE OF CORRECTION

PATENT NO. : 5,737,445
DATED : April 7, 1998
INVENTOR(S) : Jane E. Oppenlander, Kent C. Loomis, David M. Brudnoy and Arthur J. Levy It is certified that error appears in the above-identified patent and that said Letters Patent is hereby corrected as shown below:

In column 8, line 53, change "FIG. 8 or figure V's" to -- figure-8 or figure-V --.

In column 11, line 27, add -- features -- after "detecting".

In column 11, line 38, change "know" to -- known --.

In column 12, line 7, delete the comma "," after "computing".

Signed and Sealed this

Sixteenth Day of June, 1998

Attest:

BRUCE LEHMAN

Attesting Officer

Commissioner of Patents and Trademarks